March 1, 1955 E. S. BOERNER Plant Pat. 1,357
ROSE PLANT
Filed June 4, 1954
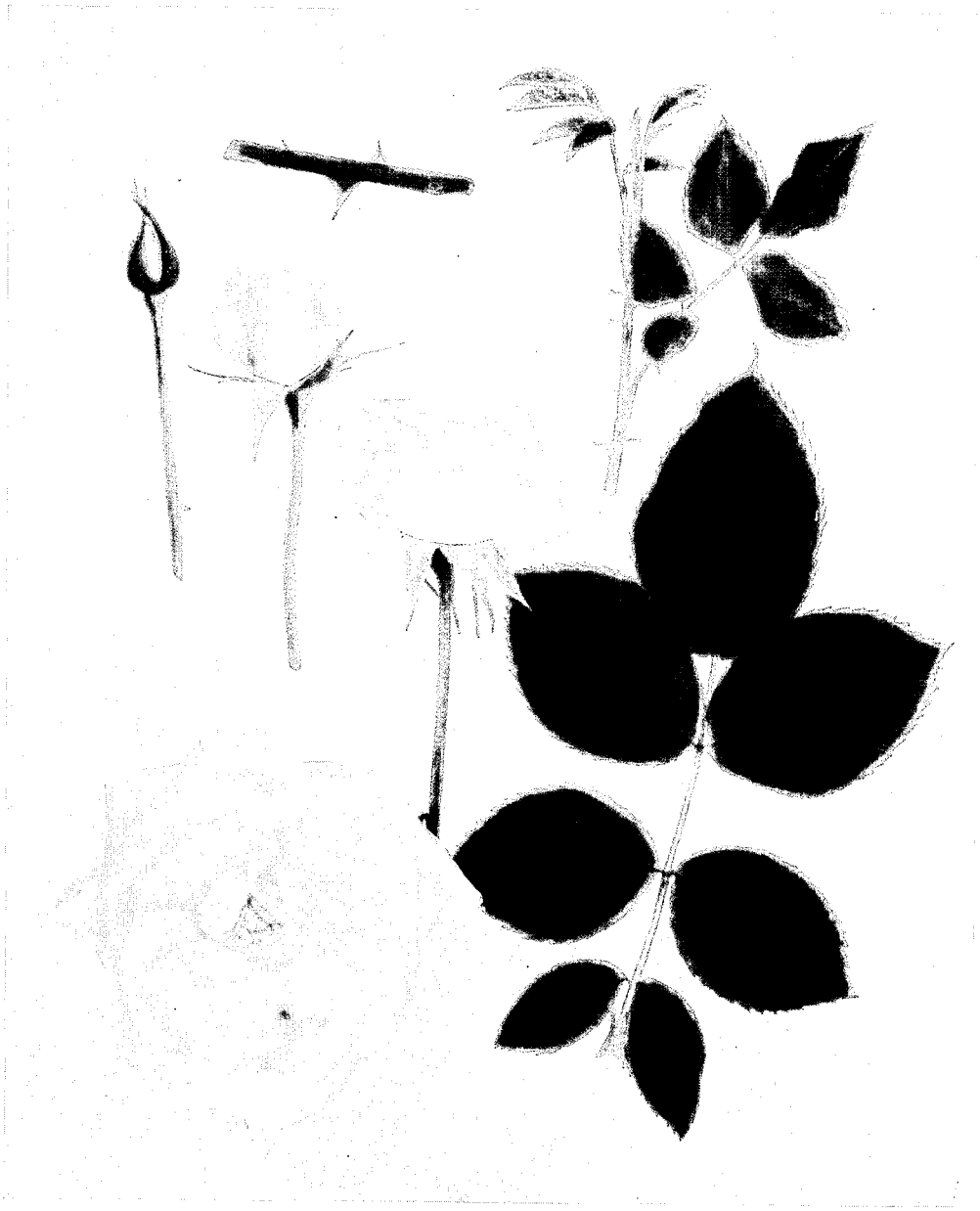
Inventor
E. S. Boerner
By: Robb & Robb
Attorneys.

United States Patent Office

Plant Pat. 1,357
Patented Mar. 1, 1955

1,357

ROSE PLANT

Eugene S. Boerner, Newark, N. Y., assignor to Jackson & Perkins Company, Newark, N. Y., a corporation of New York Application June 4, 1954, Serial No. 434,688

1 Claim. (Cl. 47—61)

The present invention relates to a new and distinct variety of rose plant of the large-flowered polyantha class, which was originated by me by crossing the variety "Geranium Red" (Plant Patent No. 811) with the variety "Fashion" (Plant Patent No. 789).

The primary objective in making the aforementioned cross was to obtain a new variety of rose plant which bears flowers in a new range of color, combined with some of the fragrance like that of the blooms of the parent "Geranium Red," and still further combined with the hardiness and foliage value of the parent "Fashion." These objectives were fully achieved, as evidenced by the distinctive Rose Doree general color tonality, lightly overcast with scarlet, of the flowers of my new variety, which color was not heretofore available under greenhouse conditions, the unusual combination of Sweet Briar and Geranium fragrance of the flowers of my new variety, the rapid production of flowers under greenhouse conditions, the hardiness of the plants, their abundant foliage and their habit of retaining their foliage to the ground. These characteristics represent a distinctive and unique combination for a rose of this class, and definitely differentiate the new variety from its parents, as well as from all varieties of which I am aware.

Asexual reproduction of my new variety by budding at Newark, New York, and also at Pleasanton, California, shows that the foregoing characteristics and distinctions come true to form and are established and transmitted through succeeding propagations.

The accompanying drawing shows typical specimens of the flowers, foliage and stems of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Geranium Red."
*Pollen parent.*—"Fashion."
Classification:
*Botanic.*—Large-flowered polyantha.
*Commercial.*—Floribunda.

FLOWER (Observations made from specimens grown in a greenhouse at Newark, New York, in the early part of the month of August, and in the early morning.)

Blooming habit: Recurrent—continuous; in greenhouse, the blooms repeat in from 20% to 30% less time than the average rose.
Bud:
*Size.*—Large.
*Form.*—Pointed ovoid; is not affected by wet or hot weather.
*Color.*—When sepals first divide—Rose Red, Plate 12. When petals begin to unfurl—Scarlet Red, Plate 1. When half blown: inside of petals—Rose Doree, Plate 1, light overcast with Scarlet, Plate 1; reverse of petals—Rose Doree, Plate 1, lightly overcast with Rose Red, Plate 12.
*Sepals.*—Branched; curl back when petals begin to unfurl. Color: inside—Kildare Green, Plate 31; outside—Light Cress Green, Plate 31.
*Calyx.*—Color—Light Elm Green, Plate 17.

Shape — funnel. Size — small. Aspect—smooth. Odor when rubbed—none.
*Peduncle.* — Length — medium. Aspect — rough. Strength—erect; slender. Color—Light Bice Green, Plate 17.
*Opening.*—Opens up well; is not affected by adverse weather conditions.
Bloom:
*Size.*—Medium. Average size when fully expanded—from 3 inches to 3½ inches.
*Borne.*—Several together and in pyramidal clusters.
*Stems.*—Medium length; strong.
*Form (when first open).*—High-centered. Permanence—retains its form to the end, but outer petals curl back.
*Petalage.*—Double (full but open center). Number of petals under normal conditions—from 25 to 30.
*Color.*—Center of flower—Rose Doree, Plate 1, lightly overcast with Scarlet, Plate 1. Outer petals—Begonia Rose, Plate 1. Base of petals (aiglet)—Primrose Yellow, Plate 30. Inside of petals—Rose Doree, Plate 1, lightly overcast with Scarlet, Plate 1. Reverse of petals—Eosine Pink, Plate 1, lightly overcast with Rose Red, Plate 12. General tonality from a distance—Rose Doree, Plate 1, lightly overcast with Scarlet, Plate 1.
*Discoloration.*—General tonality at end of first day—Rose Doree, Plate 1, lightly overcast with Scarlet, Plate 1. Second day—Rose Doree, Plate 1, lightly overcast with Scarlet, Plate 1. Third day—Begonia Rose, Plate 1, lightly overcast with Scarlet, Plate 1.
Petals:
*Texture.*—Thick; is not affected by wet or hot weather.
*Appearance.*—Inside—satiny. Outside—shiny.
*Form.*—Oval.
*Arrangement.*—Irregular.
*Petaloids in center.*—Few; small.
*Persistence.*—Drop off cleanly.
*Fragrance.*—Strong. Nature—combination of Sweet Briar and Geranium fragrance.
*Lasting quality.*—On the plant—very long. As cut flowers—very long.

GENITAL ORGANS

Stamens, anthers: Medium size; few; regularly arranged around styles. Color—Mikado Orange, Plate 3.
Stamens, filaments (threads): Medium length. Color—Barium Yellow, Plate 16.
Pollen: Color—Cream Color, Plate 16.
Styles: Bunched; uneven length; short; thin.
Stigmas: Color—Naples Yellow, Plate 16.
Ovaries: All enclosed in calyx.
Hips: None.
Seeds: None.

PLANT

Form: Bush.
Growth: Vigorous; upright; bushy.
Foliage: 5 to 7 leaflets.
*Size.*—Medium.
*Quantity.*—Abundant; completely covers plant.
*Color.*—New foliage: upper side—Yellowish Oil Green, Plate 5, lightly overcast with Oxblood Red, Plate 1, under side—Yellowish Oil Green, Plate 5, overcast with Oxblood Red, Plate 1. Old foliage: upper side—Cedar Green, Plate 6; under side—Light Cress Green, Plate 31.
*Shape.*—Oval pointed.
*Texture.*—Upper side—leathery. Under side—rough.
*Ribs and veins.*—Ordinary.
*Edge.*—Serrated (saw-toothed).
*Serration.*—Both double and single; small.
*Leaf stem.*—Color—Dark Vinaceous, Plate 27. Under side—prickles.
*Stipules.*—Long; smooth.

Wood:

*New wood.*—Color—Lettuce Green, Plate 5, lightly overcast with Carmine, Plate 1. Bark—smooth.

*Old wood.*—Color—Spinach Green, Plate 5. Bark—smooth.

Thorns:

*Thorns.*—Quantity: on main stalks from base—ordinary; on laterals from stalk—ordinary. Form—narrow base; medium length; some straight and some hooked downward. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by the distinctive color of its flowers, the combined Sweet Briar and Geranium fragrance of its flowers, its rapid production of flowers under greenhouse conditions, the hardiness of its plant, its abundant foliage, and the habit of its plant in retaining the foliage to the ground.

No references cited.